United States Patent [19]

Plattier et al.

[11] 3,970,682

[45] July 20, 1976

[54] NOVEL CYCLOPENTANONE ODORIFEROUS AGENT

[75] Inventors: Marcel Plattier, Antibes; Paul José Teisseire, Grasse, both of France

[73] Assignee: Societe Anonyme Roure Bertrand DuPont, Paris, France

[22] Filed: Jan. 11, 1973

[21] Appl. No.: 322,748

[30] Foreign Application Priority Data

Jan. 18, 1972 France .............................. 72.01510

[52] U.S. Cl. .............................. 260/468 K; 252/522; 260/514 K; 260/586 R

[51] Int. Cl.² .............................. C07C 69/74

[58] Field of Search .................... 260/468 K, 514 K

[56] References Cited

UNITED STATES PATENTS

| | | | |
|---|---|---|---|
| 3,158,644 | 11/1964 | Demole et al. | 260/468 |
| 3,288,833 | 11/1966 | Demole | 260/468 |
| 3,754,016 | 8/1973 | Oberhansli | 260/468 |

FOREIGN PATENTS OR APPLICATIONS

| | | | |
|---|---|---|---|
| 490,313 | 7/1970 | Switzerland | 260/468 |

*Primary Examiner*—Robert Gerstl
*Attorney, Agent, or Firm*—Wallenstein, Spangenberg, Hattis & Strampel

[57] ABSTRACT

The novel compound methyl [2-n-propyl-3-keto-cyclo-pent-l-yl]-acetate which is a valuable odoriferous agent is disclosed together with process for its preparation and methods of using it in perfumes, cosmetics and other products. It is noteworthy that the cis isomer possesses olfactory advantages over the trans isomer.

3 Claims, No Drawings

NOVEL CYCLOPENTANONE ODORIFEROUS AGENT

DETAILED DESCRIPTION OF THE INVENTION

The present invention is concerned with the novel compound methyl [2-n-propyl-3-keto-cyclopent-1-yl]-acetate, having the formula

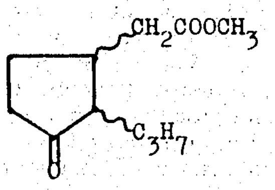

(I)

This ester of formula (I) exists in two stereoisomeric forms in which the substituents exist in cis and trans configurations, as indicated in the formula (I) by wavy lines.

The ester of formula (I) may be prepared either by a. catalytically hydrogenating methyl [2-n-propyl-3-keto-cyclopent-1-en-1-yl]-acetate or c. methylating the acid having the formula

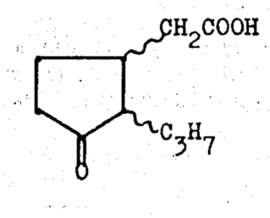

(VII)

The catalytic hydrogenation according to process variant (a) may conveniently be effected using conventional hydrogenation catalysts such as palladium or rhodium on carbon, platinum, platinum oxide, Raney nickel or Raney cobalt. The catalyst is conveniently used in an amount of 1 to 10% by weight based on the weight of starting material.

The hydrogenation procedures generally give a product containing a major proportion of the trans isomer having the formula

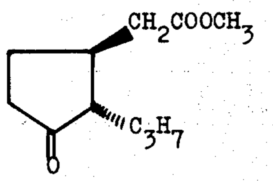

(II)

However, the hydrogenation may also be modified to obtain a product containing a major proportion of the cis isomer. This result can be attained by effecting the hydrogenation in the presence of an aluminium derivative. In general the use of an aluminium derivative in the hydrogenation can give a product containing more than 85% of the cis isomer having the formula

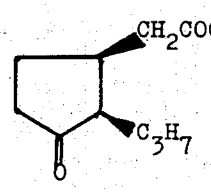

(III)

It is preferred to use an aluminium alcoholate as the aluminium derivative in the hydrogenation, both for the reasons of accessibility and ease of use. The aluminium alcoholate may be added to the reaction mixture as such, or in the form of reagents which form an aluminium alcoholate in situ, for example using a mixture of an alkyl aluminium and an alcohol.

When an aluminium alcoholate is used it is preferred to use aluminium methylate in order to avoid a transesterification reaction taking place between the alcohol of the aluminium alcoholate and the methyl group of the starting substance (methyl [2-n-propyl-3-keto-cyclopent-1-en-1-yl]-acetate) or its hydrogenated derivative of formula (I). For the same reason, where a separate solvent is added it is preferred to use methanol as the solvent.

The amount of aluminium derivative added is not critical. In general it is preferred to use about 1 gram atom of aluminium per mole of methyl [2-n-propyl-3-keto-cyclopent-1-en-1-yl]-acetate used as starting material.

The catalytic hydrogenation is advantageously effected under a pressure of from 3 to 10 kg/cm$^2$ and at a temperature of from 30° to 80°C.

The cis isomer of methyl [2-n-propyl-3-keto-cyclopent-1-yl]-acetate of formula (III) may if desired be epimerised to give the trans isomer corresponding to formula (II) by heating in the presence of a base such as sodium methylate.

The methylation of the acid of formula (VII) may be effected by conventional means to give the ester of formula (I). However, it is preferred to prepare the acid of formula (VII) in situ, by hydrolysing and decarboxylating a dialkyl malonate derivative of formula

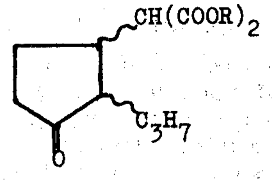

(IV)

wherein R represents a lower alkyl group, and then methylating the acid so obtained to give the compound of formula (I). The hydrolysis and decarboxylation reaction may be carried out in a conventional manner. The hydrolysis can be effected in an acidic or alkaline medium. However it is preferable to effect the hydrolysis using water, under pressure and in a neutral medium.

The treatment with water to effect the hydrolysis and the decarboxylation, is conveniently effected at a temperature of from 120° to 300°C and preferably from 140° to 250°C. The reaction is conveniently effected using about the same weight of water as of dialkyl malonate of formula (IV). The reaction is normally effected in an autoclave which has been previously purged of air.

In the formula (IV) R may conveniently be a lower alkyl group having 1 to 4 carbon atoms and preferably represents methyl or ethyl.

The dialkyl malonate derivative of formula (IV) may be prepared by the addition of a malonate of formula $CH_2(COOR)_2$ (V)

wherein R has the meaning given above, to the 2-n-propyl-2-cyclopentenone having the formula

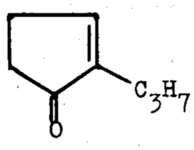

(VI)

The malonate addition is conveniently effected in the presence of a base such as sodium tert. amylate.

The compounds of formula (I) possess a prominent floral odour and may accordingly be used in the preparation of odoriferous compositions. They can be used for the preparation of perfumes and also for the perfuming of such products as toilet waters, cosmetics, washing powders and liquids, as well as many other products. The proportions in which the compounds of formula (I) can be used are conventional. In the preparation of perfumes and concentrates for the preparation of toilet waters, they may be used in an amount of 1 to 20% by weight.

The odour of compounds of formula (I), whilst being generally floral in nature, also have jasmin, lemon and magnolia notes. The odour of the cis isomer is more powerful and more fragrant than that of the trans isomer and the cis isomer accordingly constitutes a preferred feature of the invention. Further, the odour of compounds of formula (I) is distinctly more powerful than that of homologues having a longer alkyl side chain, namely: the corresponding n-butyl, isobutyl, amyl, isoamyl and n-hexyl compounds.

The invention will now be illustrated with reference to the following Examples. Unless indicated otherwise, all the parts are by weight.

EXAMPLE 1

Into a 1 liter flask purged with dry nitrogen, there is introduced 210 ml of anhydrous methanol followed by 63.2 g of aluminium triisobutyl over thirty minutes. The resulting solution is refluxed for one hour. After cooling, the solution is introduced into an autoclave with 6.5 g of 5.3% palladium on carbon. 58.8 g (0.30 mole) of methyl[2-n-propyl-3-keto-cyclopent-1-en-1-yl]-acetate is added. The autoclave is closed, shaken to homogenise the mass and heated to 40°C. Hydrogen is then introduced under a pressure of 10 kg/cm² until no further hydrogen absorption occurs. After cooling, the mass is filtered to separate the catalyst, poured into water and extracted with petroleum ether (3 × 100 ml). The petroleum ether solution is washed to neutrality and distilled. 53 g of crude product are thus obtained which are rectified under reduced pressure. 43.8 g of methyl [2-n-propyl-3-keto-cyclopent-1-yl]-acetate is thus obtained, presenting the following characteristics:

$b.p._{0.1} = 77°–80°C$; $n_D^{15} = 1.4627$; (yield 75%)

According to gas chromatography estimation the product contains more than 85% of cis isomer.

| | | |
|---|---|---|
| Infra-red spectrum: | | (in $cm^{-1}$) |
| ν (C=O) | | 1735 |
| δ ($CH_2$) in α to a C=O | | 1405 |
| ν (C—O) | | 1170, 1190, 1255 |
| N.M.R. Spectrum: | | (in p.p.m.) |
| 0.90 (t) | $CH_3$ at the end of a chain | |
| 2.70 | multiplet complex 1H | |
| 3.62 (s) | | O—$CH_3$ |

EXAMPLE 2

10 g of the cis product prepared by the method of Example 1 are refluxed with 100 ml of a normal solution of sodium methylate in methanol for one hour. After cooling, the mass is poured into water and extracted with petroleum ether (3 × 50 ml). The petroleum ether solution is washed to neutrality and then distilled. 9.5 g of crude product are obtained which are rectified under reduced pressure. $b.p._{0.1} = 92°–94°C$. According to chromatographic estimation the product contains more than 90% of the trans isomer of methyl [2-n-propyl-3-keto-cyclopent-1-yl]-acetate.

| | | |
|---|---|---|
| Infra-red spectrum | | (in $cm^{-1}$) |
| ν(C = O) | | 1740 |
| δ($CH_2$) in α to a C = O | | 1410 |
| ν(C - O) | | 1170, 1195 |
| bands at 1260, 1230, 1015 and 990 | | |
| N.M.R. spectrum | | (in p.p.m.) |
| 0.88 (t) | $CH_3$ at the end of a chain | |
| 3.63 (s) | | O - $CH_3$ |

The invention is further illustrated by the following Examples of formulations comprising the compounds of the invention, in which all parts are by weight.

| Example A<br>Fougére perfume | |
|---|---|
| 140 | Benzyl acetate |
| 80 | Linalyl acetate |
| 60 | Bergamot peel oil extra |
| 140 | Lavander oil Laragne 50% |
| 280 | Linalol |
| 20 | Galbanum oil N/Distillation, 10% in ethyl phthalate |
| 20 | Geranium Bourbon oil |
| 60 | Vetiver Bourbon oil |
| 20 | Amyl salicylate |
| 20 | Benzoin resinoid No. 1 |
| 60 | Coumarin |
| 100 | Trans-methyl[2-n-propyl-3-keto-cyclopent-1-yl]-acetate |
| 1000 | |

| Example B<br>Cologne concentrate | |
|---|---|
| 60 | Lavander oil 40% |
| 290 | Lemon peel oil extra |
| 330 | Bergamot peel oil extra |
| 30 | Vervain oil Grasse |
| 10 | Essence of oil of bitter-orange flowers, Grasse |
| 50 | Hydroxycitronellal 100% |
| 70 | Linalol |
| 10 | Oak moss absolute A |
| 30 | Vetiveryl acetate |
| 20 | Musk ketone |
| 100 | Methyl-cis[2-n-propyl-3-keto-cyclopent-1-yl-acetate |
| 1000 | |

What is claimed is:

1. Methyl [2-n-propyl-3-keto-cyclopent-1-yl]-acetate.

2. The acetate of claim 1 in the form of its cis isomer.

3. The acetate of claim 1 in the form of its trans isomer.

* * * * *